United States Patent
Holsing et al.

(10) Patent No.: US 12,099,149 B2
(45) Date of Patent: *Sep. 24, 2024

(54) ENDOBRONCHIAL CATHETER SYSTEM AND METHOD FOR RAPID DIAGNOSIS OF LUNG DISEASE

(71) Applicant: Veran Medical Technologies, Inc., St. Louis, MO (US)

(72) Inventors: Troy L. Holsing, Golden, CO (US); Mark Hunter, St. Louis, MO (US); Christopher Lee, St. Louis, MO (US)

(73) Assignee: Veran Medical Technologies, Inc., St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/357,205

(22) Filed: Jul. 24, 2023

(65) Prior Publication Data

US 2024/0027595 A1  Jan. 25, 2024

Related U.S. Application Data (63) Continuation of application No. 16/705,684, filed on Dec. 6, 2019, now Pat. No. 11,754,694.

(Continued)

(51) Int. Cl.
*A61B 8/12* (2006.01)
*A61B 1/267* (2006.01)
(Continued)

(52) U.S. Cl.
CPC ........ *G01S 7/52036* (2013.01); *A61B 1/2676* (2013.01); *A61B 8/085* (2013.01);
(Continued)

(58) Field of Classification Search
CPC ......... A61B 8/12; A61B 8/445; A61B 1/2676; G01S 7/52036
See application file for complete search history.

(56) References Cited

U.S. PATENT DOCUMENTS 7,796,789 B2  9/2010  Salgo et al.
8,611,984 B2  12/2013  Greenburg et al.
(Continued)

FOREIGN PATENT DOCUMENTS

CN  102846339 A  1/2013
CN  113164161 A  7/2021
(Continued)

OTHER PUBLICATIONS

Feb. 25, 2020 PCT Search Report (Serial No. PCT/US19/64951).
(Continued)

*Primary Examiner* — Colin T. Sakamoto
(74) *Attorney, Agent, or Firm* — Schwegman Lundberg & Woessner, P.A.

(57) ABSTRACT

A medical device and its method of use includes a catheter, at least two electromagnetic sensing coils located within the distal tip of the catheter, and a multi-element planar ultrasound transducer array located within the distal tip of the catheter and configured to transmit and receive ultrasonic energy. The device also includes an imaging system coupled to the ultrasound transducer and is used for creating an image of tissue in a first target plane that extends orthogonally from the catheter body. The medical device also includes a backscatter evaluation system for use in receiving and evaluating the acoustic spectral characteristics of tissues within a second target area within the first target plane.

10 Claims, 7 Drawing Sheets

Related U.S. Application Data (60) Provisional application No. 62/776,667, filed on Dec. 7, 2018.

(51) Int. Cl.

| | |
|---|---|
| *A61B 8/00* | (2006.01) |
| *A61B 8/08* | (2006.01) |
| *A61B 34/20* | (2016.01) |
| *A61M 25/01* | (2006.01) |
| *G01S 7/52* | (2006.01) |
| *G01S 15/89* | (2006.01) |
| *G06T 7/00* | (2017.01) |
| *A61B 10/04* | (2006.01) |
| *A61M 25/09* | (2006.01) |

(52) U.S. Cl.
CPC .............. *A61B 8/12* (2013.01); *A61B 8/4254* (2013.01); *A61B 8/445* (2013.01); *A61B 8/469* (2013.01); *A61B 8/5207* (2013.01); *A61B 34/20* (2016.02); *A61M 25/01* (2013.01); *G06T 7/0012* (2013.01); *A61B 8/4494* (2013.01); *A61B 8/463* (2013.01); *A61B 2010/045* (2013.01); *A61B 2034/2051* (2016.02); *A61M 2025/09183* (2013.01); *G01S 15/8918* (2013.01); *G01S 15/8922* (2013.01); *G01S 15/8997* (2013.01); *G06T 2207/10132* (2013.01); *G06T 2207/30061* (2013.01); *G06T 2207/30096* (2013.01)

(56) References Cited

U.S. PATENT DOCUMENTS

| | | | |
|---|---|---|---|
| 10,877,136 | B2 | 12/2020 | Moradi et al. |
| 2007/0106147 | A1 | 5/2007 | Altmann et al. |
| 2009/0299186 | A1 | 12/2009 | Waters et al. |
| 2010/0063393 | A1 | 3/2010 | Moradi et al. |
| 2010/0152566 | A1 | 6/2010 | Rains et al. |
| 2010/0234724 | A1 | 9/2010 | Jacobsen et al. |
| 2011/0207997 | A1 | 8/2011 | Greenburg et al. |
| 2012/0011414 | A1 | 1/2012 | Nitta |
| 2012/0130247 | A1 | 5/2012 | Waters et al. |
| 2013/0338477 | A1 | 12/2013 | Glossop et al. |
| 2016/0008636 | A1 | 1/2016 | Warnking |
| 2016/0331343 | A1 | 11/2016 | Hunter et al. |
| 2016/0331468 | A1 | 11/2016 | Lee et al. |
| 2016/0374562 | A1 | 12/2016 | Vertikov |
| 2017/0079519 | A1 | 3/2017 | Sung et al. |
| 2017/0258439 | A1 | 9/2017 | Jasperson et al. |
| 2017/0319772 | A1 | 11/2017 | Krimsky |
| 2017/0354395 | A1 | 12/2017 | Lupotti et al. |
| 2018/0189947 | A1 | 7/2018 | Tadayyon et al. |
| 2018/0221566 | A1 | 8/2018 | Ohnmacht et al. |
| 2018/0289323 | A1 | 10/2018 | Labyed et al. |
| 2019/0142528 | A1 | 5/2019 | Vertikov |
| 2019/0247127 | A1 | 8/2019 | Kopel |
| 2020/0178788 | A1 | 6/2020 | Waters |
| 2020/0178931 | A1 | 6/2020 | Hunter et al. |
| 2022/0268907 | A1 | 8/2022 | Hunter et al. |

FOREIGN PATENT DOCUMENTS

| | | | |
|---|---|---|---|
| CN | 113164162 | A | 7/2021 |
| JP | 2005110833 | A | 4/2005 |
| JP | 2006255014 | A | 9/2006 |
| JP | 2007068918 | A | 3/2007 |
| JP | 2009066429 | A | 4/2009 |
| JP | 2009207926 | A | 9/2009 |
| JP | 2011521730 | A | 7/2011 |
| JP | 2011245326 | A | 12/2011 |
| JP | 2012125579 | A | 7/2012 |
| JP | 2013517039 | A | 5/2013 |
| JP | 2013176559 | A | 9/2013 |
| JP | 2013179859 | A | 9/2013 |
| JP | 2013244408 | A | 12/2013 |
| JP | 2014161598 | A | 9/2014 |
| JP | 2016104192 | A | 6/2016 |
| JP | 2018008089 | A | 1/2018 |
| JP | 2018099259 | A | 6/2018 |
| JP | 2018191779 | A | 12/2018 |
| JP | 7408658 | B2 | 12/2023 |
| JP | 7410148 | B2 | 12/2023 |
| JP | 2024038018 | A | 3/2024 |
| WO | WO-2013125475 | A1 | 8/2013 |
| WO | WO-2017205373 | A1 | 11/2017 |
| WO | WO2018116892 | A1 | 6/2018 |
| WO | WO-2020118190 | A1 | 6/2020 |
| WO | WO-2020118193 | A1 | 6/2020 |

OTHER PUBLICATIONS

Jul. 27, 2022 International Office Action (Serial No. 19893633.8).
Sep. 28, 2022 USPTO Office Action (U.S. Appl. No. 16/705,684).
Kawasaki, An IntegratedBackscatter Ultrasound Technique for the Detection of Coronary and Carotid Atherosclerotic Lesions, Sensors, vol. 15, Issue 1, pp. 979-994.
Fumitaka et al., Relationship Between Qualitativ Analysis of Lung Tumors Using Integrated Backscatter-Intravascular Ultrasound, IB-IVUS and Pathological Diagnosis, European Respiratory Society 22nd Annual Congress, Vienna, Austria, Sep. 1-5, 2012. vol. 40 Issue Supp. 56, abst 1697, Pub p. 4402.
Apr. 4, 2023 International Office Action (Serial No. 2021-531329).
"U.S. Appl. No. 16/705,684, Non Final Office Action mailed Sep. 28, 2022", 23 pgs.
"U.S. Appl. No. 16/705,684, Notice of Allowance mailed May 1, 2023", 9 pgs.
"U.S. Appl. No. 16/705,684, Response filed Jan. 23, 2023 to Non Final Office Action mailed Sep. 28, 2022", 7 pgs.
"U.S. Appl. No. 16/705,684, Response filed Jun. 28, 2022 to Restriction Requirement mailed May 12, 2022", 4 pgs.
"U.S. Appl. No. 16/705,684, Restriction Requirement mailed May 12, 2022", 9 pgs.
"U.S. Appl. No. 16/705,705, Examiner Interview Summary mailed May 3, 2022", 2 pgs.
"U.S. Appl. No. 16/705,705, Non Final Office Action mailed Sep. 23, 2021", 15 pgs.
"U.S. Appl. No. 16/705,705, Notice of Non-Compliant Amendment mailed Mar. 18, 2022", 5 pgs.
"U.S. Appl. No. 16/705,705, Preliminary Amendment filed Jan. 15, 2020", 2 pgs.
"U.S. Appl. No. 16/705,705, Response filed Jan. 14, 2022 to Non Final Office Action mailed Sep. 23, 2021", 8 pgs.
"U.S. Appl. No. 17/742,752, Non Final Office Action mailed Mar. 14, 2024", 9 pgs.
"Chinese Application Serial No. 201980080960.4, Office Action mailed Feb. 22, 2024", with machine translation, 16 pgs.
"Chinese Application Serial No. 201980081027.9, Office Action mailed Nov. 15, 2023", with machine translation, 18 pgs.
"Chinese Application Serial No. 201980081027.9, Response filed Apr. 1, 2024 to Office Action mailed Nov. 15, 2023", w/ english claims, 15 pgs.
"European Application Serial No. 19893633.8, Response filed Jan. 24, 2022 to Communication pursuant to Rules 161(2) and 162 EPC mailed Jul. 14, 2021", 11 pgs.
"European Application Serial No. 19893633.8, Response filed Sep. 22, 2022 to Communication pursuant to Rules 70(2) and 70a(2) EPC mailed Aug. 17, 2022", 19 pgs.
"European Application Serial No. 19893635.3, Extended European Search Report mailed Jul. 27, 2022", 12 pgs.
"European Application Serial No. 19893635.3, Response filed Jan. 13, 2022 to Communication pursuant to Rules 161(2) and 162 EPC mailed Jul. 14, 2021", 7 pgs.
"European Application Serial No. 19893635.3, Response filed Nov. 16, 2022 to Communication pursuant to Rules 70(2) and 70a(2) EPC mailed Aug. 17, 2022", 13 pgs.

(56) References Cited

OTHER PUBLICATIONS

"International Application Serial No. PCT/US19/64951, PCT Search Report mailed Feb. 25, 2020", 3 pgs.

"International Application Serial No. PCT/US2019/064951, International Preliminary Report on Patentability mailed Jun. 17, 2021", 8 pgs.

"International Application Serial No. PCT/US2019/064951, Written Opinion mailed Feb. 25, 2020", 6 pgs.

"International Application Serial No. PCT/US2019/064958, International Preliminary Report on Patentability mailed Jun. 17, 2021", 7 pgs.

"International Application Serial No. PCT/US2019/064958, International Search Report mailed Feb. 25, 2020", 2 pgs.

"International Application Serial No. PCT/US2019/064958, Written Opinion mailed Feb. 25, 2020", 5 pgs.

"Japanese Application Serial No. 2021-531329, Office Action mailed Apr. 4, 2023", w/ English Translation, 8 pgs.

"Japanese Application Serial No. 2021-531329, Office Action mailed Aug. 1, 2023", with English translation, 5 pgs.

"Japanese Application Serial No. 2021-531329, Response filed Jun. 5, 2023", with machine translation, 4 pgs.

"Japanese Application Serial No. 2021-531330, Notification of Reasons for Refusal mailed Sep. 5, 2023", w/ English Translation, 6 pgs.

"Japanese Application Serial No. 2021-531330, Office Action mailed Apr. 18, 2023", with English Translation, 11 pgs.

"Japanese Application Serial No. 2021-531330, Response filed Jul. 12, 2023 to Office Action mailed Apr. 18, 2023", with machine translation, 13 pgs.

"Japanese Application Serial No. 2021-531330, Response filed Nov. 7, 2023 to Notification of Reasons for Refusal mailed Sep. 5, 2023", with machine translation, 25 pgs.

Bridal, S. L, et al., "Milestones on the road to higher resolution, quantitative, and functional ultrasonic imaging", Proceedings of the IEEE, IEEE. New York, US, vol. 91, No. 10, (Oct. 1, 2003), 1543-1561.

Mizoguchi, T., et al., "Envelope Statistics and Backscattered Power-Spectrum Analysis of Rat Livers with High-Frequency Annular Array", 2018 IEEE International Ultrasonics Symposium (IUS), IEEE, (2018), 1-4.

U.S. Appl. No. 16/705,705, filed Dec. 6, 2019, Percutaneous Catheter System and Method for Rapid Diagnosis of Lung Disease.

U.S. Appl. No. 17/742,752, filed May 12, 2022, Percutaneous Catheter System and Method for Rapid Diagnosis of Lung Disease.

U.S. Appl. No. 16/705,684 U.S. Pat. No. 11,754,694, filed Dec. 6, 2019, Endobronchial Catheter System and Method for Rapid Diagnosis of Lung Disease.

"Chinese Application Serial No. 201980080960.4, Response filed Jun. 24, 2024 to Office Action mailed Feb. 22, 2024", w/ english claims, 14 pgs.

"Chinese Application Serial No. 201980081027.9, Decision of Rejection mailed Jul. 13, 2024", w/o English Translation, 6 pgs.

"Chinese Application Serial No. 201980081027.9, Response filed Jul. 5, 2024 to Office Action mailed May 12, 2024", w/ english claims, 12 pgs.

"Japanese Application Serial No. 2023-215898, Notification of Reasons for Refusal mailed Jun. 18, 2024", w/ English translation, 8 pgs.

ENDOBRONCHIAL CATHETER SYSTEM AND METHOD FOR RAPID DIAGNOSIS OF LUNG DISEASE

CROSS-REFERENCE TO RELATED CASES

This application is a continuation application claiming priority to U.S. application Ser. No. 16/705,684, filed on Dec. 6, 2019, which is a utility application claiming priority to provisional application Nos. 62/776,677 and 62/776,667, of which both were filed on Dec. 7, 2018, and whose entire contents are incorporated herein by reference.

FIELD OF THE INVENTION

A medical device catheter system integrating and providing to a user, electromagnetic navigation/location information and ultrasonic imaging and spectral backscatter evaluation information to a user, for use within the lung of a patient to provide a multimode basis for the diagnosis of cancer. The catheter system may be delivered to the lung via an endobronchial access device. Post evaluation, a therapy may be supplied through the endobronchial access device, providing a compact and efficient intervention, combining both diagnosis and treatment in a single session. Although disclosed in the context of lung cancer treatment the methodology is useful for other lung diseases as well.

BACKGROUND OF THE INVENTION

Current Standard for Lung Cancer Diagnosis

At present conventional cancer protocols call for the collection of physical samples (biopsy) of suspected tissue uncovered during routine examination (X-ray, CT). The biopsy samples are sent to a laboratory for microscopic evaluation and it is the laboratory pathologist who declares the pathology of the sample making the diagnosis of the disease.

Next the patient and his physician select an appropriate treatment regime, which may include surgical resection, chemotherapy, or ablation in the case of lung cancer. If the tissue presents as advanced lung cancer, then palliative and hospice care are indicated. If the tissue presents a case of chronic obstructive pulmonary disease (COPD) or other disorder an appropriate treatment regime will be selected. If the tissue is normal, then no intervention is required.

This traditional diagnostic methodology occurs over several medical intervention sessions that may need to be repeated to verify diagnostic features of the disease, which is undesirable. This traditional methodology also has low diagnostic yield. Many disease cases are missed especially in early stage lung diseases when they are the most readily treated. Also, occasionally, a misdiagnosis results in unnecessary intervention.

Current Technologies Used for Assessing Lung Disease

The application of electromagnetic navigation (EM) to lung bronchoscopy began in the early 1990s. Veran Medical Technologies has developed a set of catheter systems that may be used with a bronchoscope or through the chest wall to accurately target and reach very small tissue masses. Biopsy tools may be delivered to the target mass through the catheter system to collect a physical sample of tissue for analysis.

This technology is described in detail U.S. Pat. No. 8,696,549 entitled Apparatus and Method for Four Dimension Soft Tissue Navigation in Endoscopic Applications. This document is incorporated by reference herein.

By way of brief overview, the EM navigation feature begins with a pre-operative CT scan of the lung indexed to the electromagnetic navigation system. A model of the lung space is created and tracked through time so that the position of the EM device within the body is seen within the computational model space. With the position or location of the EM sensors known in real time computations can be carried out to indicating the exact location of location of the device for physical biopsy. In general, a preoperative Computed Tomographic X-Ray (CT) scan is used to build a navigation model of the airways within the patient. Electromagnetic sensors (EM) sensors on the indwelling catheter are very small and provide location and orientation information for the catheter tip in three space (3D). The Veran system also provides a fourth dimension of time varying tracking information. Respiratory tracking is available in the Veran system and this is effective in altering the apparent position of the probe in the virtual display to match the physical location of the EM sensors as they move with the body's respiratory motion, which is very useful in the present device. The benefit of 4D tracking in the present invention is the additional precision that permits re-accessing very small volumes of tissue located within difficult structures within the lung For purposes of the present invention the ability to translate a known position in three space and to accurately reference this known location into an image space created from CT or other imaging modalities allows precise knowledge of the exact location under ultrasonic evaluation, and permits both physical biopsy and potentially therapy to precisely the same location, thus making small nodules treatable.

At present well known devices that apply ultrasonic imaging to lung bronchoscopy instruments are offered by several manufacturers. These Endo-Bronchial Ultrasound Systems (EBUS) allow the operator to look outside of the airways. There are two types of EBUS. Radial EBUS and linear EBUS. The typical field of view is intentionally quite large, and quite deep, to survey the maximum amount of tissue possible. The image with its anatomic detail, is typically used by the physician for navigation. Targets of interest are defined solely by the image characteristics and accessed by biopsy tools delivered to the target site through the EBUS catheter.

Clinical applications of conventional ultrasound incorporate many imaging modes, such as gray-scale "B-mode" imaging to display echo amplitude in a scanned plane; M-mode imaging to track motion at a given fixed location over time; duplex, color, and power Doppler imaging to display motion in a scanned plane; harmonic imaging to display non-linear responses to incident ultrasound; elastographic imaging to display relative tissue stiffness; and contrast-agent imaging with contrast agents to display blood-filled spaces or with targeted agents to display specific agent-binding tissue types. A less well-known ultrasonic technology is called quantitative ultrasound or (QUS), which analyzes the distribution of power as a function of frequency in the received echo signals backscattered from tissue. QUS exploits the resulting spectral parameters to characterize and distinguish among tissues.

SUMMARY OF THE INVENTION

In the view of the inventors a set of acoustic measures along with patient medical history can be used to declare a tissue sample cancerous. This evaluation is expected to be as accurate and on par with conventional pathology evaluation.

It is possible to add artificial intelligence system to combine data from several sources. For example, another potential imaging technology involves applying AI techniques such as Convolutional Neural Networks at various stages of the CT and US imaging pipeline to characterize tissue based upon training dataset. This AI assisted evaluation of image data may speed the overall diagnosis, which is desirable.

The catheter and associated systems of this invention allow targeted tissue to be accessed and identified and characterized in situ during the intervention. This diagnostic data is taken all at the same time and at the same location. This synoptic data set can be combined with other data and conventional medical judgment to reach a treatment decision immediately. The approximate target tissue location is reached in a conventional fashion by navigation through a bronchoscope following a lung model based upon and created from pre-op CT scan. The user manipulates the catheter and electromagnetic (EM) navigation is used to approach the target tissue location through visualization of the lung tissues in the model image space presented to the physician on a monitor. The location information from the navigation system shows the physician where in the derived lung model he is located. Ultrasonic imaging (US) is then used to define a first target plane or a first target volume of the tissue of interest and its precise location. Next the user defines a reduced version of this target volume containing a homogenous sample of tissue. This second reduced target plane or reduced target volume is selected so as to excludes irrelevant anatomic structures and produce an image plane or image volume that represents a homogeneous sample of suspected tumor tissue. The second reduced target is evaluated using what amounts to an acoustic biopsy by implementing QUS techniques. The overall catheter system allows for the placement of a physical biopsy sampling tool. This tool, for example a needle or brush, is then placed at the same identical target site that was evaluated acoustically and a tissue sample taken from the same tissue, such as a lymph node or other target tissue of interest, subjected to the acoustic biopsy.

As suggested above, the ultrasound system has two modes of operation. A first imaging mode displaying slicewise a relatively large first target area and a second quantitative spectral evaluation mode selecting backscattered radiation from a second reduced target area.

The ultrasound imaging system provides a controlled view around the catheter distal tip. The preferred embodiment of the ultrasound transducer is a planar array fixed into position within the distal tip of the catheter. The planar array may be used in a synthetic aperture mode constructing a displayed image plane formed from data taken a several locations at several times while the catheter body is stationary. It is possible to move the catheter translate from a first location to a second nearby location. Catheter motion may be used alone to exclude anatomic structures form the second reduced target area. The motion of the catheter creates a swept volume for use in image contraction or backscatter evaluation.

Typically, the field of view of the ultrasound transducer will be 60 degrees or less, but as suggested above it may be rotated or translated mechanically or manipulated electronically to control the size of the field of view. The depth or range of the field may also be limited in contrast to the typical EBUS system where a large view of extensive tissue is desired. Usually the US view will encompass several tissue types. Medical judgment is used to tune and to position the catheter system near the target tissue to isolate the target tissue of interest for acoustic biopsy from other anatomic features such as blood vessels and the like. In this fashion medical expertise selects a first target area encompassing the suspected tumor tissue. Next a subset of the initial first target volume is selected for backscatter analysis. This second reduced target area will be selected to be free of extraneous anatomic structures and provide a relatively homogenous tissue sample to provide backscatter suitable for spectral evaluation.

With the position of the acoustic biopsy noted by the EM location portion of the EM navigation system an integrated biopsy sample device may be directed to the acoustic biopsy location. This needle tip placement can be done with very high precision as it is calculated with knowledge from the EM sensor 4D location information.

Thus, and in practice the US system is used to image a volume of tissue, called the first target area, and then the operator manipulates the catheter system to isolate a second reduced target area to contain tissue of interest within the smaller field of view of the quantitative mode of ultrasound sensor operation. With the tissue isolated the acoustic backscattered radiation is evaluated to discern the nature of the tissue. By using QUS tools the very small sample is effectively subjected to an "acoustic biopsy" or "sonic biopsy" that is performed in situ, and at a known location that can be re-accessed to provide a therapy if required.

Furthermore, QUS can be used to analyze the tumor stroma and microvasculature nature to provide parameters related to cell death and/or apoptosis to provide confirmation or monitoring data of therapies such as chemotherapy, brachytherapy, cytotoxic agents (drugs) or ablation. This analysis can provide interim feedback of a tumor's response to therapy using parameters such as effective scatter diameter and effective acoustic concentration. The heterogeneity of a tumor or tissue stiffness can be analyzed by evaluating a nodule from multiple different directions and determining the depth of penetration of the ultrasound signal.

With the ability to create a 3D or 4D ultrasound image of the nodule. The user is able to compute both a nontextured and texture parameters for the 3D or 4D image. Nontexture features such as size, shape and location descriptors relative to adjacent structures (pleura, fissures, vessels, etc.) can be defined in ultrasound space. Additionally, texture-based features such a pixel intensity histogram and run-length (contiguous similar grey levels or RF levels) and co-occurrence to define a metric of fine to coarse tissue. Co-occurrence metrics such as contrast, energy, homogeneity, entropy, mean and maximum probability can be used to characterize the tissue in the nodule, Images can be decomposed in orthogonal components to provide wavelet features for these images. Kernels can be applied to reflect or highlight a specific or different type of structure in the images. Applying multiple kernels based on multiple orientations can be used to characterize the tissue of the nodule. AI techniques may be used to augment texture-based classification in the image domain.

The exemplary US system uses piezoelectric transducers fabricated using modern micro-machining techniques. In general, the array of individual transducer elements are addressable and may be activated individually. Typically, the array will include elements sized to operate a particular resonant frequency. Although a single frequency array is possible it is expected that the array will have elements operable at least two frequencies. The elements may be considered to have a diameter and depth sometimes called a drum size, and like a drum each element will have a resonant frequency associated with its geometry. In general, there are many fabrication alternatives for producing ultrasonic transducer arrays including PZT, pMUT or cMUT based devices. It is expected that any of these could be used to collect the tissue information. There are trade-offs to be considered and it is desirable to maximize the fractional bandwidth of the devices. Having a common or consistent characterization for different tissue types can either be achieved through a calibration of the transducer to a known performance characteristic or implemented using repeatable performance provided from an integrated circuit such as a pMUT. This normalization is key to providing repeatable identification of the tissue. The system can allow for varying frequencies of the ultrasound transducer and therefore capture tissue data at multiple frequencies (4 to 50 MHz). Imaging may be optimized for 20 MHz while the acoustic biopsy may be acquired at a different frequency that will typically be higher.

Current US systems have the limitation of decreasing resolution in the lateral direction which creates a varying signal depending on the distance the tissue of interest is from the ultrasound transducer. The array construction of the ultrasound transducer provides increased, consistent resolution in the lateral direction for the complete field of view (FOV) or across varying depths from the transducer.

The US system with integrated EM localization allows 3D and 4D ultrasound volumes to be collected by recording multiple ultrasound image planes and reconstructing the volume. These volumes can be respiratory gated to have multiple volumes created at the same tissue location of interest (i.e. tidal volume inspiration, tidal volume expiration, or interim states along the breathing cycle). These volumes can be at multiple states of processing from raw electrical signal data to beam formed B-mode image data for analysis.

The integrated EM sensor allows for sampling the same tissue of interest from multiple viewpoints or angles to therefore determine the variation or change based on the viewpoint. Avoiding structures such as blood vessels, fissures or surrounding infection will provide a cleaner acoustic biopsy and can be used to determine the quality of the acoustic biopsy collected based on interference from other structures.

In order to get the ultrasound transducer as close to the tissue of interest as possible it is important to miniaturize the device to be less than 2 mm in diameter and short as possible to make tight turns to maintain flexibility of the catheter through the patient's airways. In the endobronchial embodiment and at present it is envisioned to have at least 64 imaging elements but other configurations from 16 to over 256 could be operable. These multiple imaging elements are multiplexed to allow for the fewest wires possible to drive the US transducer while maintaining a frame rate of 20 to 30 frames per second.

Using the EM system and registered CT data, provides for correlated multiple modality images that can be for enhance interpretation. Additional modalities such as PET-CT can be registered to identify tissue of interest. The ultrasound image provides additional data points other than the EM system that can be used for deformation of pre-operative or intra-operative images. Not only the pathway that can be recorded as a point cloud, but a pathway volume outside the airway can be collected as part of the point cloud.

Models to estimate the probability of malignancy in patients with pulmonary nodules using clinical profile, demographic and imaging data (CT, FDG-PET, growth rate) such as the Gurney, Mayo Clinic, Herder, VA, Peking University People's Hospital, Brock University, Thoracic Research Evaluation and Treatment, and Bayesian Inference Malignancy Calculator are well known. While they do provide the physician input, they are not sufficient to definitively determine if a nodule is malignant. Additionally, radiomics has been applied to CT images to further provide a likelihood of malignancy based on the CT image data. This US system with an integrated EM capability enables the ability to register the CT and FDG-PET image data to the patient and correlate the US, CT and FDG-PET image data simultaneously at the precise location within the patient. Additionally, bronchoscopic image data (color variation of tissue) created by infrared, ultraviolet and visible light. A pressure sensor may also be integrated to provide pressure data for the tissue of interest. Another type of sensor may be included in the device for example a temperature sensor can be integrated to determine the temperature change between tissue and the tissue region of interest. An oxygen sensor can be integrated to determine changes in the oxygen levels between the tissue. Other types of sensor may be used to monitor the metabolic characteristics of the tissue. This extra sensor value may be used to help determine the presence of cancer.

It is understood that this device is not limited to the lung and may be used for multiple organs (lung, liver, kidney, prostate, soft tissue, pancreas, etc.). Pathways to get to the tissue of interest can be airways or blood vessels or direct percutaneous access, or access through a natural orifice. It may also be used for therapy confirmation as well as nodule diagnosis.

DETAILED DESCRIPTION OF REPRESENTATIVE EMBODIMENTS

Figure 1:
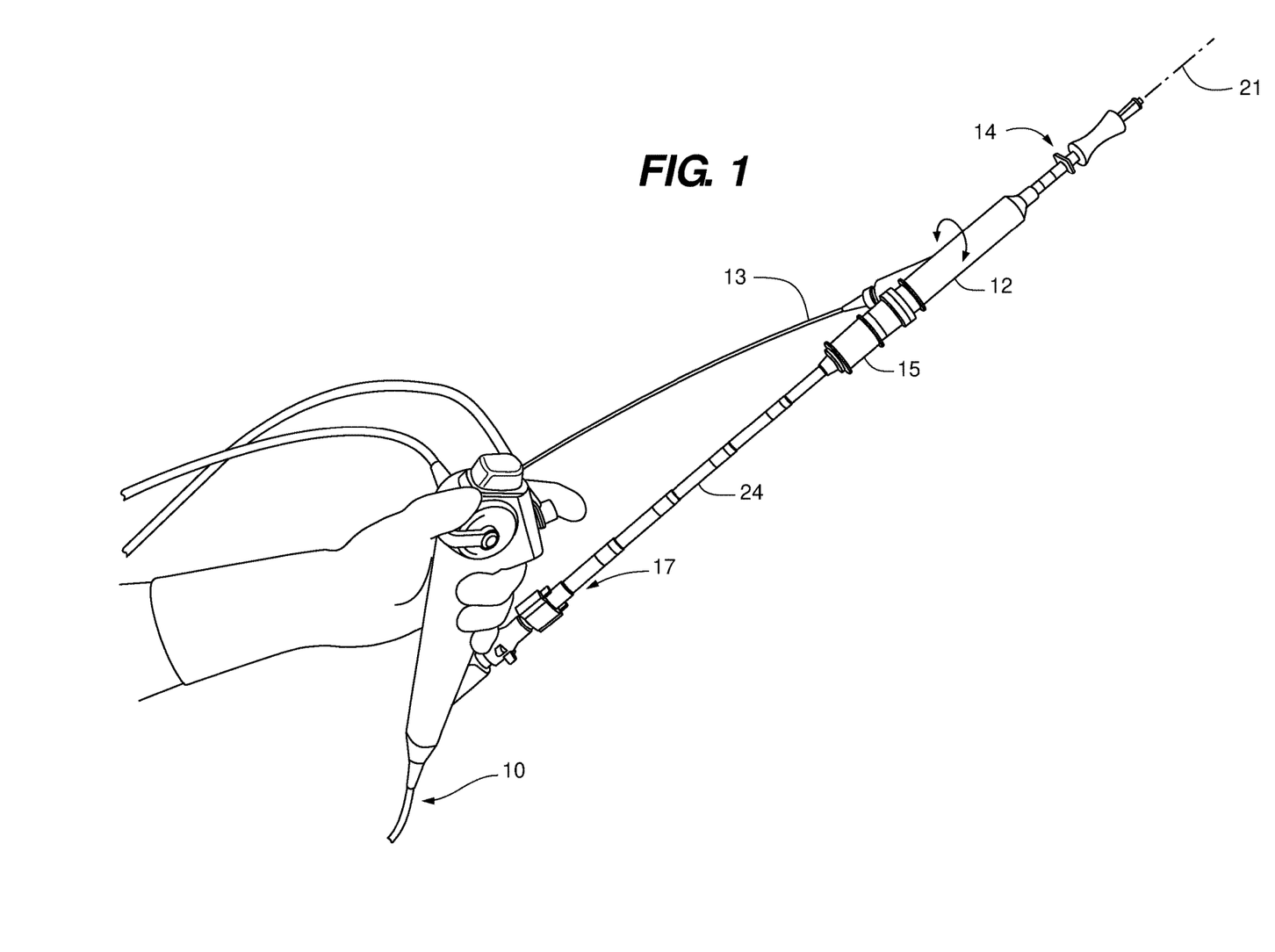
FIG. 1 is a schematic view of the context of the invention.

Turning to FIG. 1, a patient not seen is undergoing an endobronchial intervention through a scope 10. The catheter assembly 14 shown in more detail in FIG. 2 and FIG. 3 includes an elongate catheter body 18 terminating in a distal end or tip 16 and extending from a proximal grip 20 through a handle 12. The assembly is manipulated with the handle 12 and by rotation member 15. The assembly 14 is in turn inserted into the working channel 17 of the scope 10. Note that the handle can be moved independently from the scope 10 and rotational motion as indicated in the figure by rotation arrow 13 may be accomplished via manipulation of rotation member 15 with the scope 10 stationary. In this fashion the catheter system 14 is navigated into the lung (not shown) via the scope 10. The physician can maneuver the catheter system via the scope 10 and the proximal grip 20 and the handle 12.

Figure 2:
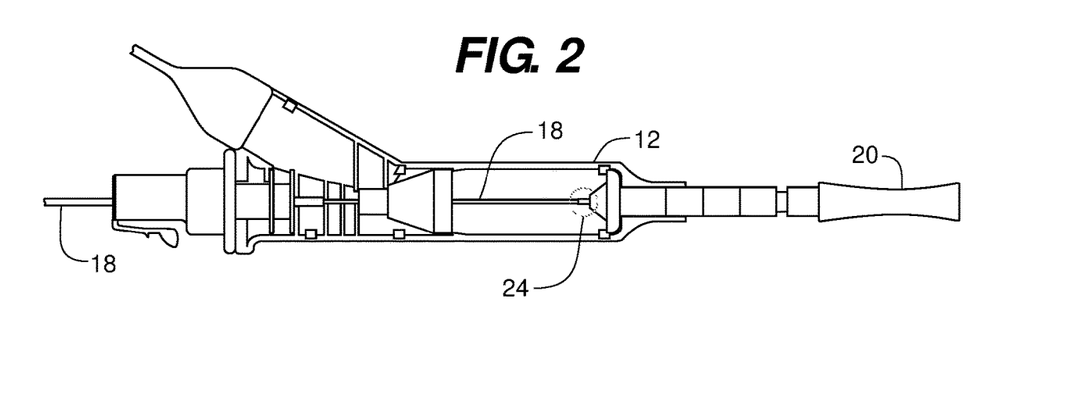
FIG. 2 is a schematic view of the proximal portion of the catheter system.
Figure 3:
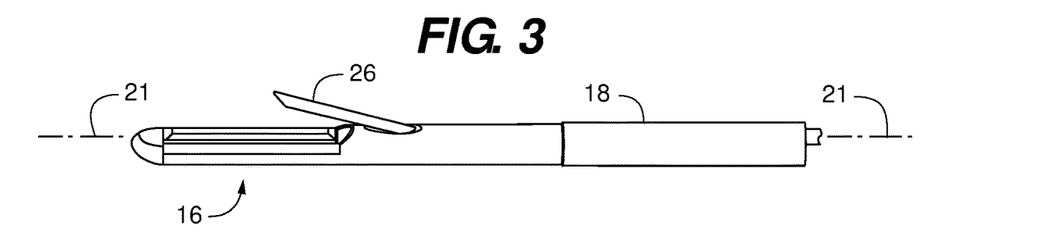
FIG. 3 is a schematic view of the distal portion of the catheter system.

FIG. 3 shows the distal tip 16 of the catheter body 18 in isolation and in more detail. The catheter body 18 extends through the handle 12 as seen in FIG. 2, and it may be adjusted with the catheter's proximal grip 20 over a small range sufficient to allow retraction into the distal end of the scope and to effect small motions to the sensors. The overall length and location of the assembly 14 within the scope 10, to accommodate scope length, is carried out with telescoping extension piece 24, while small translations of the catheter position are carried out with the handle 12 and proximal grip 20. The distal body of the catheter body 18 carries an access lumen that can be used to introduce a tool such as the needle 26 which is shown emerging from the aperture in the body 18.

Figure 4A:
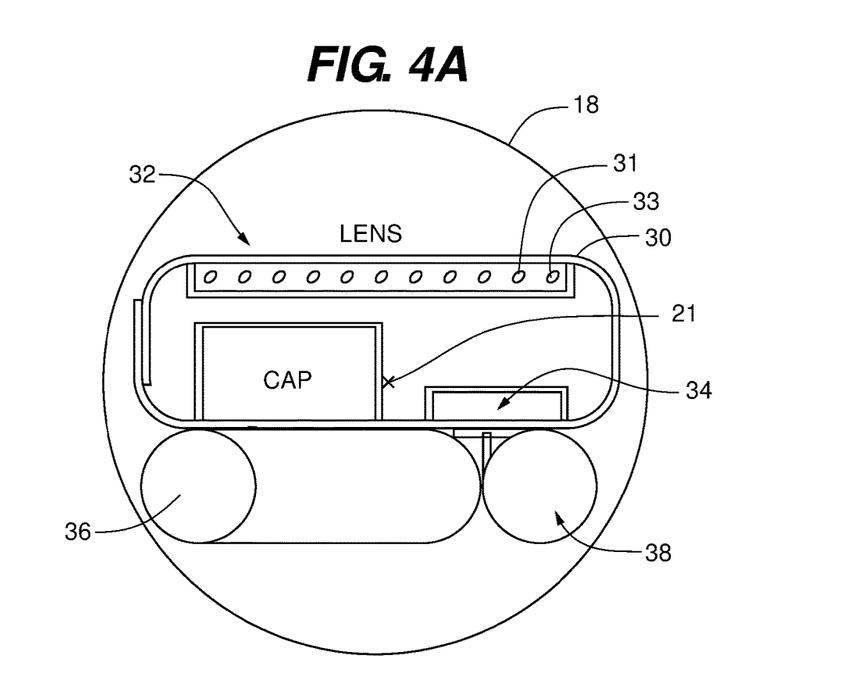
FIG. 4A is a schematic view of a cross-section taken near the distal tip of the catheter.

FIG. 4A shows a cross section of the distal tip distal to the aperture. A multi-element planar ultrasound array 30 lies within the catheter body 18, is positioned parallel to the longitudinal axis 21 of the catheter (shown in FIGS. 1 and 3) and is covered by an acoustic lens 32. An electronics package 34 is located in the tip near the EM coils shown as coil 38 and coil 36. Other packaging strategies may prove operable as well.

Figure 4B:
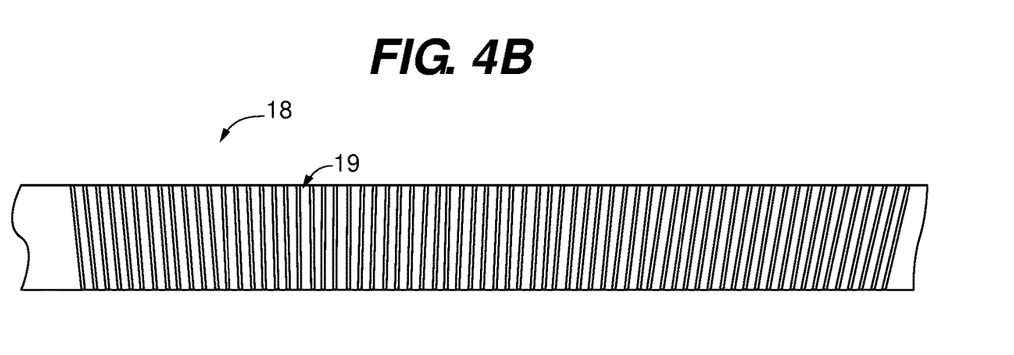
FIG. 4B is a detailed portion of a segment of the catheter body.

FIG. 4B shows a portion of the elongate catheter body 18 that may be formed of stainless steel or other material and to create and control its flexibility the tubular structure may be laser cut in a spiral pattern that permits flexibility in one or more planes. The kerf 19 of the laser cuts are oriented so as to permit flexion.

Figure 5:
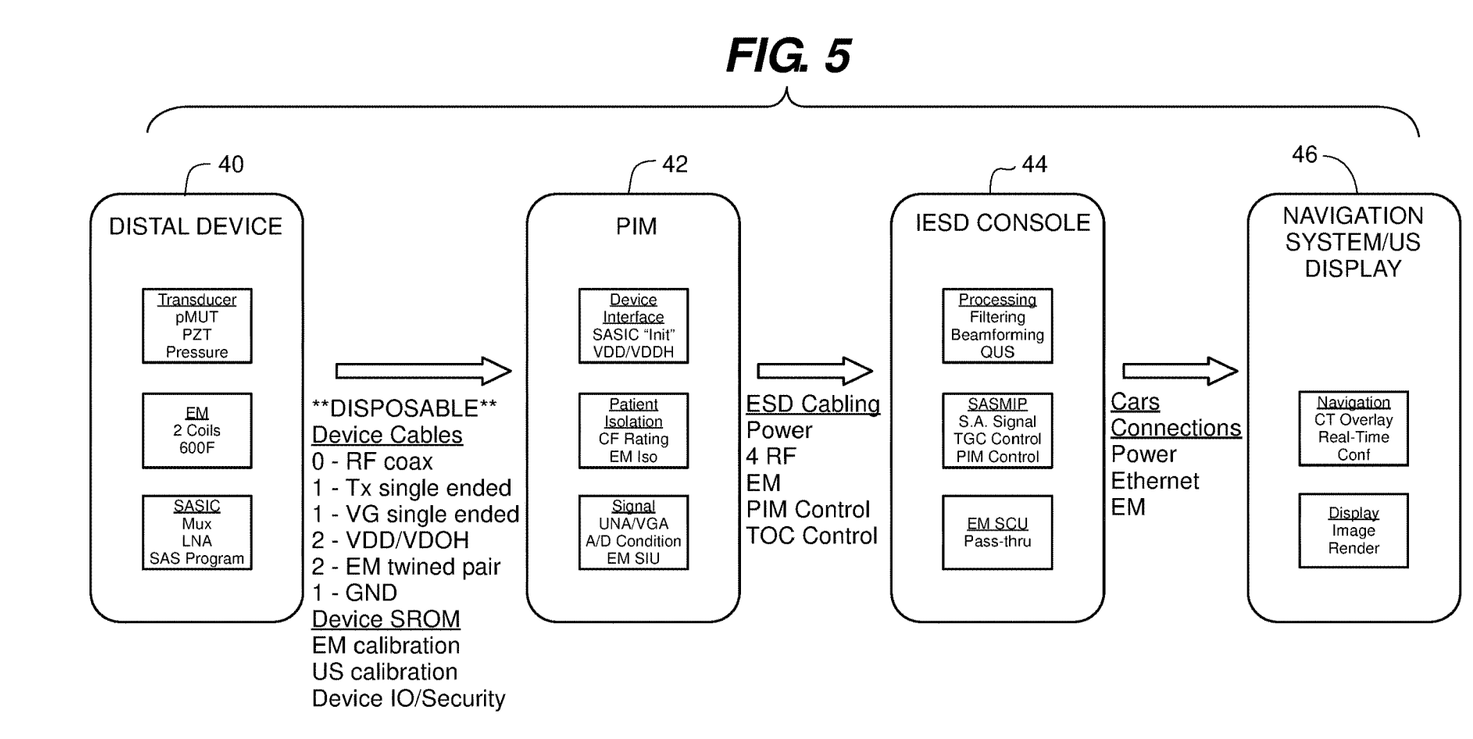
FIG. 5 is a schematic block diagram of the electronic portioning of the systems.

FIG. 5 is a partitioning of the electronic componentry of the catheter system and its accompanying imaging system and is an illustrative but not limiting version of the system in its present implementation.

The electronic package 34 of FIG. 4 will contain among other things a programmable chip to configure the array 30. A multiplexer will format and transmit data from the catheter system to the patient interface module or PIM 42, which will be hung bedside on the gurney with the patient. The PIM 42 includes electrical isolation to protect the patient and also contain power supplies for the catheter itself, A/D conversion and various buffering processes are accomplished in the PIM to improve noise performance of the catheter. In this implementation a separate "pizza box" enclosure carries dedicated hardware for the synthetic aperture beam forming and control as well as the spectral analysis of the backscattered signals for the QUS processes 44. The enclosure is coupled to the workstation-based navigation and display cart. The QUS backscatter evaluation system 44 residing in the pizza box enclosure may be separate or incorporated into the workstation 46 itself where visual images of the ultrasonic signals and analysis is displayed.

As described in brief elsewhere, the catheter body 18 carries a matrix of individually addressable piezoelectric transducers or elements fabricated into an array 30 using micromachining technology. Each element of the array, illustrated in FIG. 4A as elements 31 and 33, can be powered to emit ultrasonic energy as a spherical wave emanating from the specific transducer location, and each element in the array can function as a receiver transducing the mechanical energy of backscattered sound into an electrical signal. Once a spherical wave is launched from a given element 31, a companion transducer, such as element 33, can detect after a delay, the backscattered energy reflected off of biologic tissues. In the synthetic aperture scenario only one transducer 33 is listening to the transmitting transducer 31 element at a time.

In general pairs of elements will be activated with one element 31 functioning as a transmitter of acoustic energy and the companion element 33 functioning as a receiver. Since the elements are arrayed in space several viewpoints are present in the array. This provides much improved lateral resolution when compared to prior art approaches.

With that data stored, a next transducer in the array is activated to transmit acoustic energy and its complimentary transducer receives the backscattered return signal. With many, for example 64 transducers, at various locations, the composite of all the returned energy from all the locations can be used to form though computation an image plane orthogonal to the plane of the transducer.

It is possible to have more than one transducer pair active at a time and in the exemplary embodiment 4 channels of data are collected synchronously. The limitations are based on complexity and power dissipation and bandwidth of the data paths. Consequently, other configurations are possible and anticipated within the scope of the claims. The mathematics to pull an image in a plane from the time sequenced multiplex data that is transmitted and received at various points in space is complicated but well known and understood in the field. In general, the displayed image plane is synthesized from data taken at many locations in space taken at different times, that are collectively convolved into a single image plane hence the term synthetic aperture. If one moves the catheter along a path the synthetic aperture image plane sweeps out a volume. This is a relatively low-resolution image of a volume of tissue but can help to resolve the extent of anatomy to supplement the detection of anatomic structures such as airways, blood vessels, and the like in the 2-D first image plane area. In this regard the methodology of the invention may rely on a first target image area in a plane or rely on a 3-D volume called the first target image volume. In this later case catheter movement is used to define the first 3-D volume of target tissue.

In use there are two modes of operation for the ultrasound transducer array. In a first mode, the amplitude and envelope information from the backscattered acoustic energy is used to form an image presented to the clinician. This may be a first 2-D slice of target tissue or a 3-D volume of target tissue. In a second mode the transmitted power is reduced to select a smaller target plane or volume within the first image plane or image volume. This reduced view is called the second reduced area or slice in the event of a 2-D slice or a second reduced volume in the event of a 3-D volume. In each case the reduced view is selected to be free of anatomic detail observed in the first view. The exclusion of gross anatomic structure selects a homogenous sample for quantitative analysis. The spectra of the backscattered energy from the reduced area slice or volume is evaluated quantitatively and automatically rather than used to form an image. The image free quantitative information is used to determine if the reduced area of tissue exhibits the acoustic characteristics of cancerous tissue. The precise characteristics or the acoustics of cancer is a topic of study at the present time.

Figure 6:
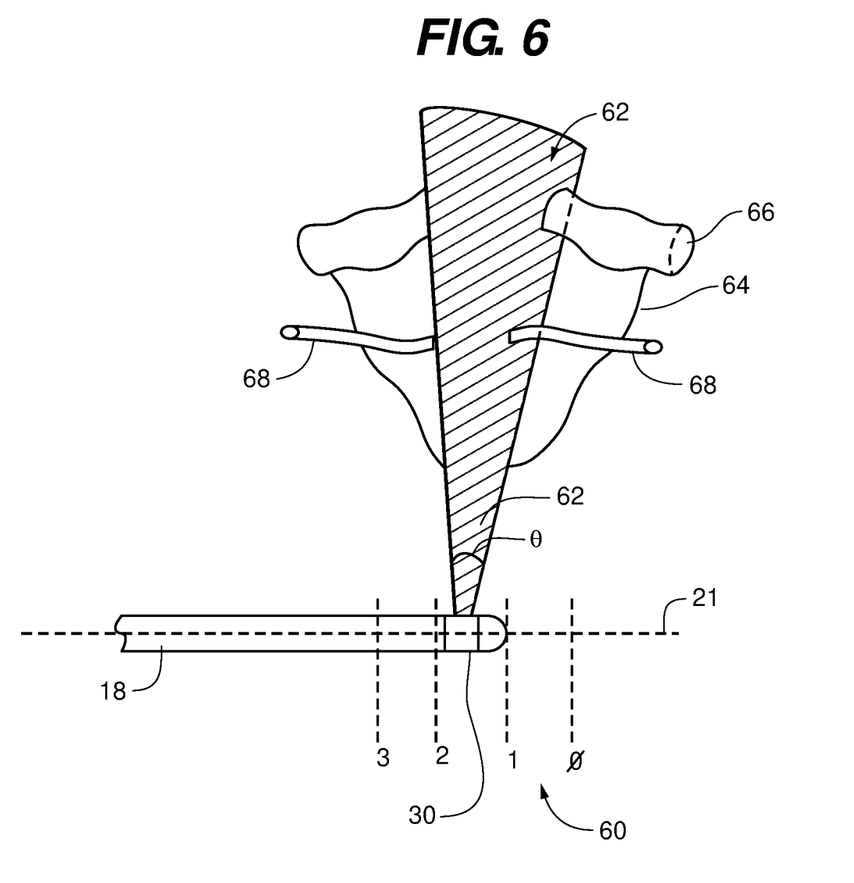
FIG. 6 is a schematic view showing the first target image plane

FIG. 6 shows the catheter body 18 with the distal tip located at position "1" marked 60 in the figure. The first target plane 62 show in light hatch is an image plane intersecting a suspected tumor mass 64 that lies near an airway 66 and is crossed by a blood vessel labeled 68 twice in the figure. This image mode ultrasound data is used to find the suspect tumor mass and to verify and note its location. To aid in the location and identification of the suspected tumor mass the catheter body 18 maybe translated along axial path 11 or rotated as indicated by rotational path 13 via rotation member 15 as seen in FIG. 1.

Figure 7:
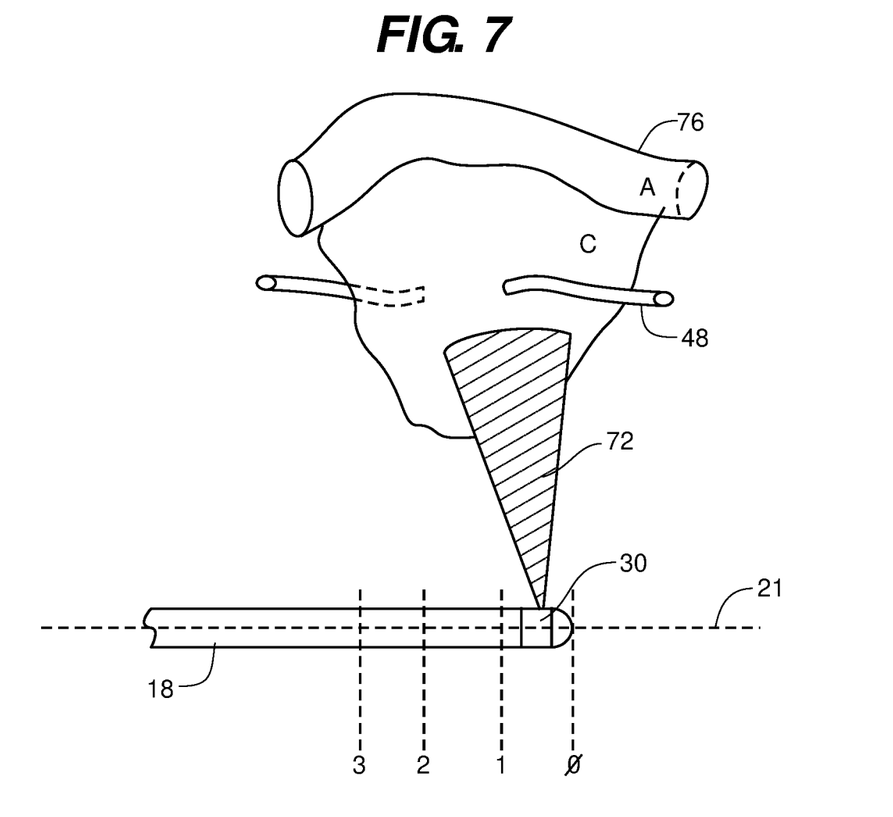
FIG. 7 is a schematic view showing the reduced second target image plane.

FIG. 7 shows the catheter body 18 repositioned or moved slightly so that the backscatter associated with reduced target plane 72 does not intersect the blood vessel or airway. This is the reduced second image plane used for backscatter evaluation for QUS. Note that the motion of the catheter may be made by the physician or different portions of the array may be activated to accomplish the same effect. In general, an automated system will select a reduced target area from the initial image in the first target plane. The automated system may form part of the OUS system shown in element 44 of FIG. 5. In general, the process will exclude image components based on contiguity and contrast to automatically remove blood vessels and airways for example. The power level of the transducers in the array may be tailored to cut out portions of the image in an automatic process or the image plane may be synthesized in a different location to exclude detected anatomic details. The ultimate goal is to provide a recommendation or diagnosis based entirely on automated evaluation of the US information.

Figure 8:
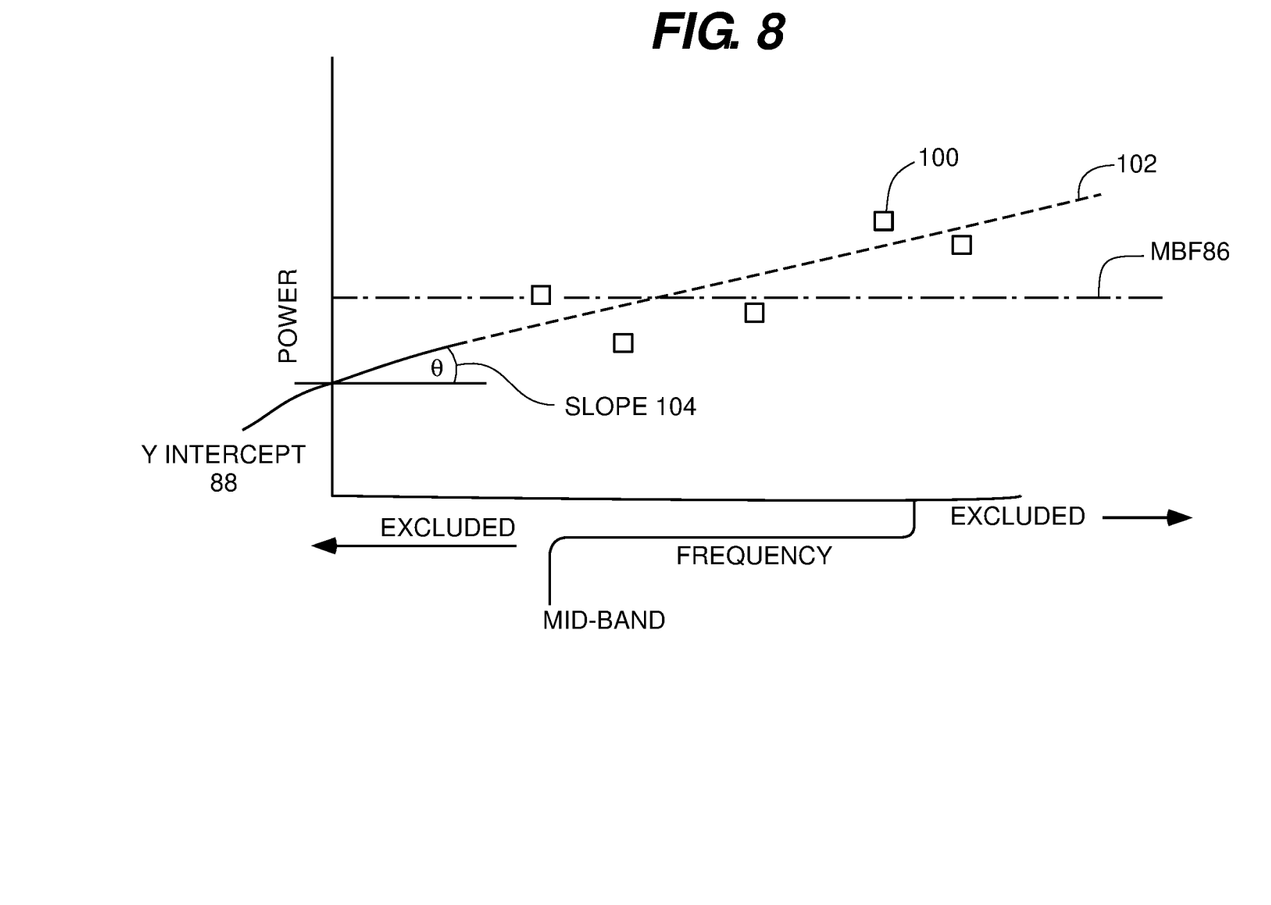
FIG. 8 is a spectral diagram showing illustrative acoustic parameters for QUS.

FIG. 8 shows a spectral graph of normalized reflected acoustic power on the Y-axis and the corresponding frequency on the X-axis. Squares typified by square 100 depict the amplitude of reflected power at the corresponding frequency. One can draw a "best fit" line 102 through the various data typified by data point 100. The slope of this line is a useful parameter and is identified on the figure at 104. The point where the best fit line 102 crosses the y axis is the Y-intercept 88. If one excludes both high and low frequencies defining a mid-band the arithmetic average of the remaining values forms the mid band fit value 86 shown on the figure.

Calibration and Alternative Embodiments.

In general, the ultrasound spectra will be normalized to perform the QUS parameters. However, the absolute energy in the reflected signal has diagnostic value alone and it is expected that the not normalized spectra will be used clinically as well. For this reason, among others, it will be important to calibrate individual catheter sensors. The ultrasound transducer technology as well as fabrication methodology results in widely varying sensitivity and other acoustic properties. It is anticipated that each sensor will be characterized during the manufacturing process to generate a compensation profile for the sensor over its entire operating range. This unique calibration table will be stored onboard the catheter is an appropriate read on memory.

It is generally preferred to have a linear planar US transducer array to carry out the inventive steps, however as an alternative the sensor could be a linear structure forming a pie shape field of view. Also, this pie shaped field of view ay be stepped around a circle either mechanically by rotational motion 13 or electronically.

An additional EM sensor may be paced in the handle and this proximal EM sensor system may be used with the EM sensor array in the distal tip to translate physician motion which affects the sensors to provide information and feedback to the physician about the orientation of the catheter system. In this version the relative motion or position of the two EM sensors along with the known geometry of the catheter allow for the computation of the location of the tip or another attribute of the catheter.

In another embodiment a method of imaging a region within a patient, using a medical device described herein is disclosed. The method comprises the following steps:

Providing the catheter assembly 14 such as is shown in FIG. 1. The catheter 14 has an elongate catheter body 18 including a proximal handle portion 12 and a distal tip portion 16 together forming the catheter assembly 14. As may be seen in FIG. 4A, there are at least two electromagnetic sensing coils 36 and 38 located within the distal tip portion 16. Turning back to FIG. 1, it is shown that the catheter assembly 14 is adapted for use through the working channel 17 of a bronchoscope 10 so as to provide providing access to the lung or other tissue of a patient.

As shown in FIG. 4A and further illustrated in FIGS. 6 and 7, a multi-element planar ultrasound transducer array 30 is located within the distal tip portion 16 of the catheter assembly 14. The array 30 is configured for the transmission and receipt of ultrasonic energy. The array 30 is positioned parallel to the axis 21 of said catheter body 18 at the catheter tip portion 16.

As is shown in FIGS. 5-7 the medical device system is further provided with an imaging system coupled to said ultrasound transducer array 30 for creating an image of tissue in a first target plane 62 extending orthogonally from said catheter body 18. A backscatter evaluation system 44 is provided to receive and evaluate the acoustic spectral characteristics of tissues located in a second reduced second target area 72, selected from the first target plane 62.

The distal tip of the medical device is navigated to a first location such as in the manner shown in FIG. 6. Here, tissue is observed in the first target plane and said second reduced target area such as in the manner shown in FIGS. 6 and. 7. The acoustic spectra of tissue observed within said second target area is analyzed. A sampling tool, such as needle 26 is deployed to targeted tissue such for example a lymph node, within said second reduced target area.

The ultrasound image data, acoustic spectra characterization data and location data illustrated in FIGS. 6-8 are all taken at the same time and the same location and displayed to a physician to inform a medical decision.

Alternatively, a method of diagnosing a region of interest within lung tissue of a patient comprises these following steps:

Passing a catheter 14 of the type shown in FIG. 1 through a bronchoscope working channel 17 to access said lung tissue. The catheter comprises an elongate catheter body 18 including an axis 21 and a distal tip portion 16. At least two electromagnetic sensing coils 36 and 38 are located within said distal tip portion, as is shown in FIG. 4A. Also positioned in the distal tip portion 16 is a multi-element planar ultrasound transducer array 30. The planar array 30 is positioned parallel to the axis 21 of said catheter body. As is shown in FIG. 6, the distal tip portion 16 of the catheter 18 is navigated to a first location proximal to the region of interest using a navigation system 46 that interacts with the two electromagnetic sensing coils 36 and 38. The system then, via the array 30, transmits first ultrasound energy into the region of interest shown in FIG. 6. The array 30 receives the first ultrasound energy and transmits it to the imaging system 46.

At the imaging system, an image is created of the region of interest shown in FIG. 6. The image will show an anatomic structure, said anatomic structure selected from a set of structures comprising airways and blood vessels. The system then identifies a target area within the image of the region of interest that does not contain the anatomic structure.

The distal tip is moved to a second location proximal to the target area using said navigation system. The array 30 then transmits a second ultrasound energy signal into the target area and the return signal is evaluated using a backscatter evaluation system 44, illustrated in FIG. 5. At the backscatter evaluation system, the acoustic spectra of the received second ultrasound energy is evaluated to extract diagnostic information for the target area of the region of interest.

The many features and advantages of the invention are apparent from the above description. Numerous modifications and variations will readily occur to those skilled in the art. Since such modifications are possible, the invention is not to be limited to the exact construction and operation illustrated and described. Rather, the present invention should be limited only by the following claims.

What is claimed is:

1. A medical device system comprising:
   a) a catheter having an elongate catheter body including a proximal handle portion and a distal tip portion together forming a catheter assembly, said catheter assembly adapted for use through a bronchoscope working channel providing access to the lung tissue of a patient;
   b) a multi-element planar ultrasound transducer array located within said distal tip portion and for transmitting and receiving ultrasonic energy in an imaging mode and an acoustic biopsy mode, in the imaging mode said ultrasonic energy having a first frequency and in the acoustic biopsy mode said ultrasonic energy having a second frequency higher than the first frequency, said planar ultrasound transducer array positioned parallel to a longitudinal axis of said catheter body at said distal tip portion;
   c) an imaging system coupled to said ultrasound transducer for creating an image of tissue in a first target area extending orthogonally from said catheter body; and
   d) a backscatter evaluation system for receiving and evaluating acoustic spectral characteristics of tissues located in a second reduced target area, selected from the first target area.

2. The medical device system of claim 1, the distal tip portion comprising an acoustic lens, the acoustic lens covering the multi-element planar ultrasound transducer array.

3. The medical device system of claim 1, further including a sampling system located proximate said distal tip, the bronchoscope defining an aperture in communication with the working channel, the aperture positioned proximal to the multi-element planar ultrasound transducer array.

4. The medical device system of claim 3, wherein the sampling system is a needle deployed from within the catheter body through the aperture.

5. The medical device system of claim 4, wherein a portion of the catheter body proximal to the aperture defines a kerf, the kerf having a spiral pattern.

6. The medical device system of claim 1, further comprising an electronics package, the electronics package is positioned within the distal tip portion adjacent to the multi-element planar ultrasound transducer array, the electronics package including a programmable chip with programming to configure the multi-element planar ultrasound transducer array.

7. The medical device system of claim 6, wherein the multi-element planar ultrasound transducer array is comprised of a plurality of individually addressable piezoelectric transducers, the plurality of individually addressable piezoelectric transducers including first elements and second elements, at least one of the first elements constructed and arranged for the transmission of the ultrasonic energy, at least one of the second elements constructed and arranged to receive the ultrasonic energy transmitted from the at least one first elements and reflected from a region of interest.

8. The medical device system of claim 7, further comprising a patient interface module, the patient interface module in communication with the catheter and providing electrical power to the catheter.

9. The medical device system of claim 8, wherein the backscatter evaluation system is in communication with the patient interface module and the imaging system.

10. The medical device system of claim 1, wherein the first frequency is 20 MHz.

* * * * *